US012611540B2

(12) United States Patent
Leonhardt et al.

(10) Patent No.: US 12,611,540 B2
(45) Date of Patent: Apr. 28, 2026

(54) MODULATION OF GROWTH DIFFERENTIATION FACTOR 10 (GDF10)

(71) Applicant: Leonhardt Ventures LLC, Mission Viejo, CA (US)

(72) Inventors: Howard J. Leonhardt, Mission Viejo, CA (US); Kelsie Leonhardt, Mission Viejo, CA (US)

(73) Assignee: LEONHARDT VENTURES LLC, Mission Viejo, CA (US)

( * ) Notice: Subject to any disclaimer, the term of this patent is extended or adjusted under 35 U.S.C. 154(b) by 624 days.

(21) Appl. No.: 18/051,425

(22) Filed: Oct. 31, 2022

(65) Prior Publication Data

US 2023/0133737 A1 May 4, 2023

Related U.S. Application Data

(60) Provisional application No. 63/274,387, filed on Nov. 1, 2021.

(51) Int. Cl.
| *A61N 1/32* | (2006.01) |
| *A61N 1/372* | (2006.01) |
| *A61M 5/142* | (2006.01) |

(52) U.S. Cl.
CPC ......... *A61N 1/326* (2013.01); *A61N 1/37205* (2013.01); *A61M 5/14276* (2013.01); *A61M 2202/07* (2013.01); *A61M 2205/05* (2013.01)

(58) Field of Classification Search
CPC ........... A61N 1/326; A61N 1/20; A61N 1/205
See application file for complete search history.

(56) References Cited

U.S. PATENT DOCUMENTS

| 8,442,653 B2 | 5/2013 | Gill |
| 9,700,596 B2 | 7/2017 | Carmichael et al. |
| 10,960,206 B2 | 3/2021 | Leonhardt et al. |
| | (Continued) | |

FOREIGN PATENT DOCUMENTS

WO     WO2020/041705     *   2/2020

OTHER PUBLICATIONS

American Heart Association, "Naturally occurring protein to block inflammatory response improved stroke recovery in mice" (Sep. 22, 2021), Medical Express (Cardiology); medicalxpress.com/news/2021-09-naturally-protein-block-inflammatory-response.html.

(Continued)

*Primary Examiner* — George R Evanisko
(74) *Attorney, Agent, or Firm* — TraskBritt

(57) ABSTRACT

Described is a low voltage, pulsed electrical stimulation device for controlling expression of growth differentiation factor 10 ("GDF10"), a useful protein, by tissues. Also described are methods of enhancing expression of GDF10 in cells, particularly a method of stimulating the expression and/or release of GDF10 in a cell having a gene encoding GDF10, wherein the method includes applying a bioelectric signal produces, as measured at the level of the target cells or tissues being stimulated 2 mA to 4 mA direct current positive to the cell (e.g., directly, indirectly, or wirelessly). Applications in the treatment of cerebral strokes, brain injuries, paralysis, brain cancer, Alzheimer's disease, dementia, anxiety, Parkinson's disease, and/or essential tremors are also disclosed.

4 Claims, 5 Drawing Sheets

(56)        References Cited

U.S. PATENT DOCUMENTS

| | | | |
|---|---|---|---|
| 2008/0208287 A1* | 8/2008 | Palermo | A61N 1/323 607/3 |
| 2019/0329033 A1* | 10/2019 | Li | A61N 1/205 |
| 2020/0000709 A1 | 1/2020 | Leonhardt et al. | |
| 2020/0289826 A1 | 9/2020 | Leonhardt | |
| 2023/0071154 A1* | 3/2023 | Leonhardt | A61N 1/36034 |

OTHER PUBLICATIONS

Chen "A potential treatment of COVID-19 with TGF-ß blockade." Int J Biol Sci. Apr. 21, 2020; 16(11):1954-1955. Doi: 10.7150/ijbs. 46891. PMID: 32398962; PMCID: PMC7211163.

Ghazavi et al. "Cytokine profile and disease severity in patients with COVID-19". Cytokine. Sep. 30, 2020; 137:155323. Doi: 10.1016/j.cyto.2020.155323. Epub ahead of print. PMID: 33045526; PMCID: PMC7524708.

Jiang et al. "A guinea pig IFNA1 gene with antiviral activity against human influenza virus infection." Front Biosci (Landmark Ed). Mar. 1, 2019; 24:790-797. PMID: 30844713.

Kennedy et al. "Impaired innate, humoral, and cellular immunity despite a take in smallpox vaccine recipients." Vaccine. Jun. 14, 2016; 34(28):3283-90. Doi: 10.1016/j.vaccine.2016.05.005. Epub May 11, 2016. PMID: 27177944; PMCID: PMC5528000.

Koti et al. "BCG vaccine and COVID-19: implications for infection prophylaxis and cancer immunotherapy." J Immunother Cancer. Jul. 2020; 8(2):e001119. Doi: 10.1136/jitc-2020-001119. PMID: 32636240; PMCID: PMC7342862.

Kumar et al. "Human Sertoli cells support high levels of Zika virus replication and persistence." Sci Rep. Apr. 3, 2018; 8(1):5477. doi: 10.1038/s41598-018-23899-x. PMID: 29615760; PMCID: PMC5883016.

Li, et al. "GDF10 is a signal for axonal sprouting and functional recovery after stroke," Nature Neuroscience, 2015; doi: 10.1038/nn.4146.

Limonta et al. "Fibroblast Growth Factor 2 Enhances Zika Virus Infection in Human Fetal Brain." J Infect Dis. Sep. 13, 2019; 220(8):1377-1387. doi: 10.1093/infdis/jiz073. PMID: 30799482; PMCID: PMC6743838.

McGowan et al. "Targeting the SphK-S1P-SIPR Pathway as a Potential Therapeutic Approach for COVID-19." Int J Mol Sci. Sep. 29, 2020; 21(19):7189. Doi: 10.3390/ijms21197189. PMID: 33003377; PMCID: PMC7583882.

Meini et al. "Intussusceptive angiogenesis in Covid-19: hypothesis on the significance and focus on the possible role of FGF2." Mol Biol Rep. Oct. 2020; 47(10):8301-8304. Doi: 10.1007/s11033-020-05831-7. Epub Sep. 12, 2020. PMID: 32920756; PMCID: PMC7486971.

U.S. Appl. No. 63/237,682, filed Aug. 27, 2021, to Leonhardt et al. for "Modulation of Brain-Derived Neurotrophic Factor (BDNF)".

Zhang et al. "Discharge may not be the end of treatment: Pay attention to pulmonary fibrosis caused by severe COVID-19." J Med Virol. Oct. 27, 2020. Doi: 10.1002/jmv.26634. Epub ahead of print. PMID: 33107641.

\* cited by examiner

| Bioelectric Stimulation Condition (20 minutes) | Fold Change |
|---|---|
| 2mA, 20 Hz, 1000 usec | 3.182146 |
| 2mA, 20 Hz, 300 usec | 1.140764 |
| 2mA, 10 Hz, 300 usec | 3.605002 |
| 3mA, DC positive | 12.38052 |
| control | 1 |

MODULATION OF GROWTH DIFFERENTIATION FACTOR 10 (GDF10)

CROSS-REFERENCE TO RELATED APPLICATION

This application claims the benefit under 35 U.S.C. § 119(e) of U.S. Provisional Patent Application Ser. No. 63/274,837, filed on Nov. 1, 2021, the contents of the entirety of which are incorporated herein by this reference.

TECHNICAL FIELD

The application relates generally to the field of medical devices and associated methods of treatment, and more specifically to methods of treatment involving the precise bioelectrical stimulation of a subject's tissue, optionally augmented with the administration of a composition comprising, among other things, stem cells and nutrients, useful to increase the expression and/or release of growth differentiation factor 10 ("GDF10") to stimulate and treat the subject, the subject's tissue(s), the subject's organ(s), and/or the subject's cells. More specifically, the application relates to a device, programmed bioelectric signaling sequences, and associated methods for the controlled expression of GDF10 via the administration of precise bioelectrical signaling sequences, useful for, among other things, delivering specific bioelectric signaling sequences for brain regeneration protein expressions on demand.

BACKGROUND

Growth differentiation factor 10 ("GDF10"), which is also known as bone morphogenetic protein 3B ("BMP-3B" or "BMP-3b"), is a protein that in humans is encoded by the GDF10 gene. GDF10 belongs to the transforming growth factor beta superfamily. In mice, GDF10 mRNA is abundant in the brain, inner ear, uterus, prostate, neural tissues, blood vessels, and adipose tissue, with low expression in spleen and liver. GDF10 mRNA is also present in bone of both adult and neonatal mice. Human GDF10 mRNA is found in the cochlea and lung of fetuses, and in testis, retina, pineal gland, and other neural tissues of adult humans.

U.S. Pat. No. 9,700,596 to Carmichael et al. (Jul. 11, 2017) for "Locally released growth factors to mediate motor recovery after stroke" (see, also, Songlin Li, et al., "GDF10 is a signal for axonal sprouting and functional recovery after stroke," *Nature Neuroscience,* 2015; doi:10.1038/nn.4146), the contents of each of which are incorporated herein by this reference, describes methods of improving recovery of a mammal after an ischemic event (e.g., stroke). In various embodiments the methods involve administering a neural growth factor into the infarct (e.g., stroke) cavity in a biocompatible hydrogel formulation. In certain embodiments, the hydrogel comprises a thiolated hyaluronan and a thiolated gelatin with an optional thiolated heparin. In certain embodiments, methods for improving recovery (e.g., motor recovery) of a mammal after cerebral ischemia involve administering a therapeutically effective amount of a brain growth factor, such as BMP 3b, to the infarct cavity in the brain of the mammal.

BRIEF SUMMARY

Described herein is a bioelectric stimulator particularly configured to modulate (e.g., upregulate) expression and/or release of growth differentiation factor 10 in cellular tissue.

Also described is a method for treating or regenerating a tissue in a subject (e.g., in an animal, mammal or human), the tissue selected from the group consisting of neural tissue, nervous tissue, muscle, heart, eye, liver, dental tissue and teeth, bone, adrenal gland, pancreas, brain, skin, and lung, the method comprising: applying a bioelectric signal to the tissue, which the bioelectric signal regulates (e.g., upregulates or downregulates) the expression and/or release of GDF10.

In certain embodiments, the described bioelectric signaling utilized to upregulate expression of GDF10 in a cell or subject tissue is combined with the co-administration of brain-derived neurotrophic factor ("BDNF"), stromal cell-derived factor 1 ("SDF1"), insulin-like growth factor 1 ("IGF-1"), Klotho, Parkin, platelet-derived growth factor ("PDGF"), ubiquitin carboxyl-terminal hydrolase isozyme L1 ("UCHL1"), neutrophil extracellular trap ("NET"), neonatal NET-inhibitory factor ("nNIF"), and/or nerve growth factor ("NGF") (and/or bioelectric signaling co-stimulation of tissue so as to upregulate expression and/or release therefrom of, for example, BDNF, SDF1, IGF1, and/or Klotho) to treat the subject's neural tissue (e.g., in the case brain treatment or regeneration after stroke). Co-administration and/or co-upregulation of BDNF, SDF1, IGF1, and/or Klotho are preferred.

BDNF, IGF1 and GDF10 have been identified as key proteins involved in brain recovery by facilitating the restoration of lost neuronal connections. SDF1 is a known stem cell homing factor. Klotho has been shown to improve cognitive function and memory in pre-clinical studies. Low klotho levels have been linked to depression and addiction as well as chronic inflammation and arterial calcification.

In certain embodiments, the therapy is combined with the down-regulation of sonic hedgehog ("SHH").

In certain embodiments (e.g., for severe cases) the herein described therapy includes repeat infusions or injections of stem cells and biologic support factors such as secretome from amniotic sourcing, bioelectrically pre-treated PRF (see, e.g., US Patent Application Publication No. 20200000709 A1 (Jan. 2, 2020) for "Combination of Bioelectric Stimulator and Platelet-Rich Fibrin for Accelerated Healing and Regeneration"), selected exosomes, nutrient hydrogel, selected alkaloids (e.g., tetraharmine), and appropriate matrix. In chronic cases, this may involve refilling an under skin implantable infusion pump daily.

Also described is a bioelectric stimulator including: a power source (e.g., battery, capacitor, AC, or other suitable source of electricity), and means for delivering an electrical signal to a subject's tissue (e.g., via electrode(s) or wirelessly). The bioelectric stimulator utilizes the electrical signal to precisely control GDF10 expression in the tissue on demand.

In certain cases, the bioelectric stimulator is programmed to produce a bioelectric signal that stimulates target tissue to express and/or release GDF10 by the target tissue by utilizing a bioelectric signal that produces 2 mA to 4 mA direct current positive polarity (as measured at the level of the cells being stimulated), preferably 3 mA, results in the upregulation of expression of GDF10. A significant increase was measured at 2 mA to 4 mA direct current positive polarity, but the largest increase occurred at 3 mA.

A preferred system includes: a bioelectric stimulator that controls/stimulates the release/production of GDF10 by a target cell or tissue. The stimulator may be associated with (e.g., connected to) the organ or tissue to be treated with a pacing infusion lead (available from Nanoscribe of Eggenstein-Leopoldshafen, Germany) or wirelessly. In certain cases, the interface with the subject's tissue may be by a conductive soft wrap.

The stimulator can be designed to externally deliver all regeneration promoting signals wirelessly to the subject's organ(s), tissue(s), and/or cells. In certain embodiments, a micro infusion pump may be included in the system to deliver other supportive substances (such as stem cells) in greater volume more quickly.

While not intending to be bound by theory, the described system utilizes precise bioelectric signaling sequences that appear to communicate with the cells, cell membranes, and DNA of the subject cells to cause the cells to produce high volumes of the growth differentiation factor 10 protein. The herein described bioelectric stimulator, system, and associated methods find use in helping in helping patients recover from cerebral strokes, brain injuries, paralysis, brain cancer, Alzheimer's disease, dementia, anxiety, Parkinson's disease, and/or essential tremors.

Tissue(s) that may be stimulated include brain, inner ear, uterus, prostate, neural tissue(s), blood vessels, adipose tissue, spleen, liver, bone, cochlea, lung, testis, retina, and pineal gland.

DETAILED DESCRIPTION

In certain embodiments, described is a low voltage, pulsed electrical stimulation device for controlling expression of Growth differentiation factor 10 ("GDF10"), a useful protein, by tissues. Also described are methods of enhancing expression of GDF10 in cells, particularly a method of stimulating the expression and/or release of GDF10 in a cell having a gene encoding GDF10, wherein the method includes applying a bioelectric signal that produces 2 mA to 4 mA direct current positive polarity (as measured at the level of the cells being stimulated), preferably 3 mA, results in the upregulation of expression of GDF10. A significant increase was measured at 2 to 4 mA direct current positive polarity, but the largest increase occurred at 3 mA. Statistically significant increases of upregulated expression of GDF10 above baseline have been achieved by stimulating fresh porcine brain tissues.

Figure 1:
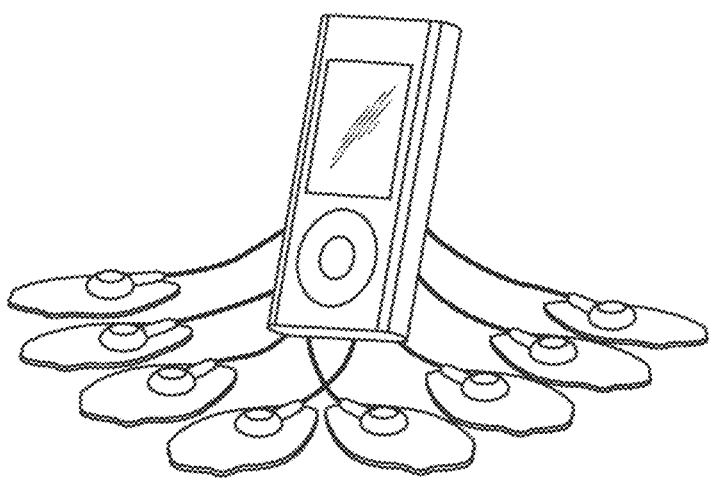
FIG. 1 depicts a programmed bioelectric stimulator for delivery to a subject connected to multiple soft conductive electrode pads.
Figure 2:
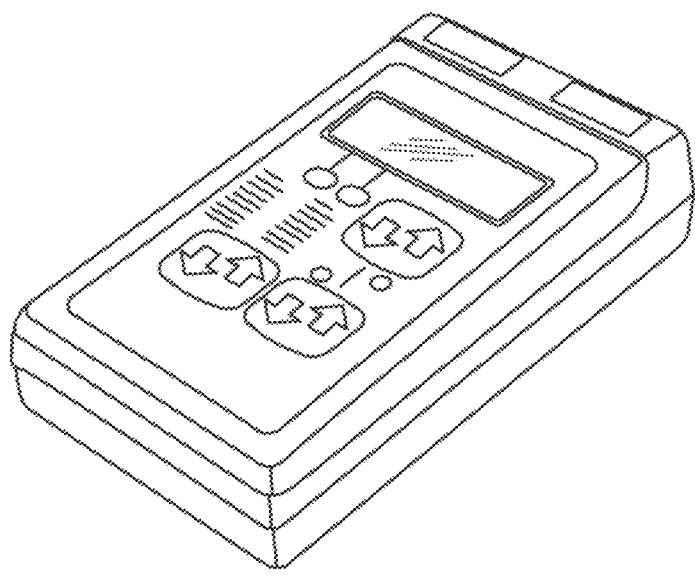
FIG. 2 depicts a programmed bioelectric stimulator as described herein.
Figure 3:
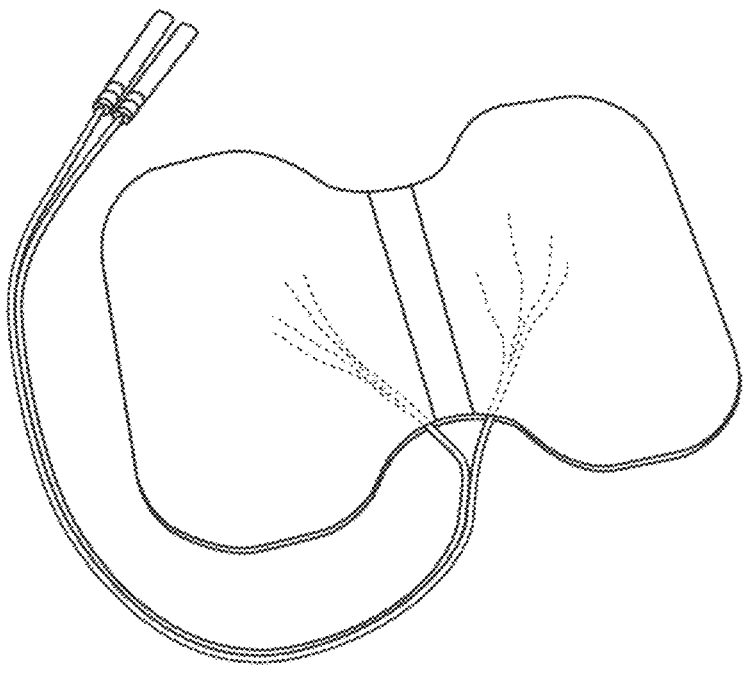
FIG. 3 depicts a conductive soft wrap for use with the system.
Figure 4:
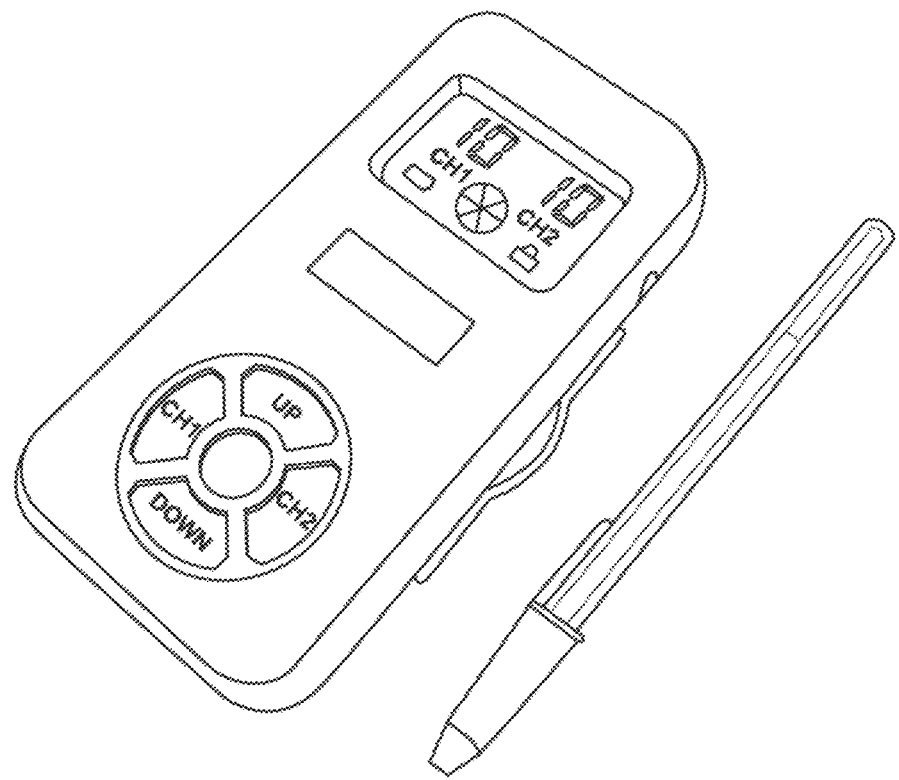
FIG. 4 depicts a programmed bioelectric stimulator depicted alongside a pen.

Referring now to FIG. 1, depicted is a stimulator for use in treating a human. The depicted device is about the size of a pen (FIG. 4) and is programmable.

A micro voltage signal generator for use herein may be produced utilizing the same techniques to produce a standard heart pacemaker well known to a person of ordinary skill in the art. An exemplary microvoltage generator is available from Mettler Electronics Corp. of Anaheim, Calif., US or HTM Electrônica of Amparo, BR. The leading pacemaker manufacturers are Medtronic, Boston Scientific Guidant, Abbott St. Jude, BioTronik and Sorin Biomedica.

Construction of the electric signal generators and pacemakers, are known in the art and can be obtained from OEM suppliers as well as their accompanying chargers and programmers. The electric signal generators are programmed to produce specific bioelectric signals to lead to specific protein expressions at precisely the right time for, e.g., optimal treatment or for tissue regeneration.

The biostimulator of FIG. 1 is depicted with multiple soft conductive electrode pads. Electrodes may be used to deliver a bioelectric signal to the subject by applying the electrodes to the subject's skin (e.g., on the skin above the thigh muscles or on the skin above the kidneys). In certain embodiments, a bioelectric stimulator is in electrical connection with a conductive soft wrap.

A bench top stimulator (e.g., a Mettler Model 240 Stimulator from Mettler Electronics of Anaheim, Calif., US) may be pre-programmed with the bioelectric signaling sequence(s) for controlling the expression and/or release of GDF10.

In some embodiments, the bioelectric signaling can further be used to modulate (e.g., upregulate) by the subject's cells the production of other molecules in addition to GDF10 and/or the recruitment of stem cells.

For example, the expression of brain-derived neurotrophic factor ("BDNF") may be upregulated as described in U.S. Patent Application Ser. No. 63/237,682, filed Aug. 27, 2021, for "Modulation of Brain-Derived Neurotrophic Factor (BDNF)" to Leonhardt et al., the contents of which are incorporated herein by this reference. For example, a bioelectric signal at 2 mA (as measured at cellular level) and 10 Hz or 100 Hz stimulation, BDNF is significantly expressed in neocortex tissue.

The expression of stromal cell-derived factor 1 ("SDF1" or "CXCL12"), a stem cell recruiting signal, may be upregulated as described in U.S. Pat. No. 10,960,206 to Leonhardt et al. (Mar. 30, 2021) for "Bioelectric Stimulator," the contents of which are incorporated herein by this reference. For example, expression of SDF1 is upregulated by the application of the following bioelectric signal to the subject's tissue: 30 Hz with a voltage of 3.5 mV, and successively alternating currents of 700 to 1500 picoamps for one minute, and again with 700 to 1500 picoamps for one minute and stimulated with current of 0.25 mA, pulse duration of 40 pulses/s, pulse width of 100 μs, and frequency of 100 Hz—each signal for 40 minutes to 8 hours a day for a duration of 7 minutes. A preferred bioelectric signal produces a biphasic/microcurrent having a frequency at 30 Hz to 40 Hz, 100 ΞS pulse width, continuous delivery, at the level of the cell.

The expression of insulin-like growth factor 1 ("IGF-1"), may be upregulated as described in the incorporated U.S. Pat. No. 10,960,206 to Leonhardt et al. For example, expression of IGF is upregulated by the application of, within 15%, 3 mV with a frequency of about 22 Hz, and a current of about 1 mA, followed by 3 mA (all voltages and amperages measured at the cellular level). A preferred bioelectric signal produces a monophasic positive/microcurrent having a frequency at 22 Hz, 50% duty pulse width, continuous delivery, at the level of the cell.

The expression of Klotho may be upregulated as described in U.S. Patent Application Publication US 20200289826-A1 to Leonhardt et al. (Sep. 17, 2020) for "Klotho Modulation," the contents of which are incorporated herein by this reference. For example, a bioelectric signal comprising a biphasic pulse at (within 15%) 20 Hz, 0.1 V (as measured at the cellular level), and a 7.8 ms pulse duration upregulates expression of Klotho in a cell or tissue. A preferred bioelectric signal produces a biphasic/microcurrent having a frequency at 20 Hz, 1000 µs pulse width, continuous delivery, at the level of the cell.

The expression of platelet-derived growth factor ("PDGF"), may be upregulated as described in the incorporated U.S. Pat. No. 10,960,206 to Leonhardt et al. (Mar. 30, 2021) for "Bioelectric Stimulator". For example, expression of PDGF is upregulated by the application of one or more of the following bioelectric signals to a cell or the subject's tissue: 3 V/cm, 10 Hz, 2 µA (0.000002 amps), and pulse duration of 0.2 ms, the application of 20 V/cm, 100 Hz, 0.25 mA (2.5e-7 amps), and pulse duration of 40 pulses/s, width of 100 µs, or the application of 20 V for 1 minute, 20 mV for 10 minutes, current of 0.25 mA, pulse duration of 40 pulses/s, pulse width of 100 µs, and frequency of 100 Hz for 5 minutes followed by 528 Hz for 3 minutes and 432 Hz for 3 minutes and 50 Hz for 3 minutes (all voltages and amperages measured at the cellular level). A preferred such bioelectric signal produces a biphasic/microcurrent having a frequency at 10 Hz, 200 µs pulse width, continuous delivery, at the level of the cell.

As previously described, in certain embodiments, administration of at least one bioelectric signal to a mammalian subject (or cell) increases the expression of interferon type 1 (IFN-1), interferon β (IFNβ), and/or sphingosine kinase 1 (SPHK1) are upregulated, and/or inhibits the expression of, AKT-1, Angiopoietin 2 (ANGPT-2), B-cell lymphoma 2 (BCL-2), chemokine (C-X-C motif) ligand 9 (CXCL9), chemokine (C-X-C motif) ligand 10 (CXCL10), basic fibroblast growth factor (FGF-β or FGF-2), leptin (LEP), transforming growth factor-beta 2 (TGF-β2), and/or transforming growth factor (TGF-β1).

For example, in treating COVID-19, IFN-1 is a potential potent candidate to improve the efficiency of vaccines and to interfere with COVID-19 activity in the already infected patient. See, e.g., Madhuri et al. "BCG vaccine and COVID-19: implications for infection prophylaxis and cancer immunotherapy." *J Immunother Cancer.* 2020 July; 8(2):e001119. Doi: 10.1136/jitc-2020-001119. PMID: 32636240; PMCID: PMC7342862; Jiang et al. "A guinea pig IFNA1 gene with antiviral activity against human influenza virus infection." *Front Biosci* (Landmark Ed). 2019 Mar. 1; 24:790-797. PMID: 30844713. Kennedy et al. "Impaired innate, humoral, and cellular immunity despite a take in smallpox vaccine recipients." *Vaccine.* 2016 Jun. 14; 34(28):3283-90. Doi: 10.1016/j.vaccine.2016.05.005. Epub 2016 May 11. PMID: 27177944; PMCID: PMC5528000.

IFNβ a cytokine belonging to the interferon family of signaling proteins, which are released as part of the innate immune response to pathogens, which are important for defense against viral infections.

With respect to SPHK1, stem cells are mobilized in presence of Covid19, and the vaccine. The relevance of stem cells mobilization has been demonstrated in the many clinical trials already performed in COVID-19 patients. See, e.g., McGowan et al. "Targeting the SphK-S1P-SIPR Pathway as a Potential Therapeutic Approach for COVID-19." *Int J Mol Sci.* 2020 Sep. 29; 21(19):7189. Doi: 10.3390/ijms21197189. PMID: 33003377; PMCID: PMC7583882.

With respect to the genes involved in angiogenesis, intussusceptive angiogenesis in Covid-19: hypothesis on the significance and focus on the possible role of FGF2. Simone et al. "Intussusceptive angiogenesis in Covid-19: hypothesis on the significance and focus on the possible role of FGF2." *Mol Biol Rep.* 2020 October; 47(10):8301-8304. Doi: 10.1007/s11033-020-05831-7. Epub 2020 Sep. 12. PMID:

32920756; PMCID: PMC7486971; Kumar et al. "Human Sertoli cells support high levels of Zika virus replication and persistence." *Sci Rep.* 2018 Apr. 3; 8(1):5477. doi: 10.1038/s41598-018-23899-x. PMID: 29615760; PMCID: PMC5883016; and Limonta et al. "Fibroblast Growth Factor 2 Enhances Zika Virus Infection in Human Fetal Brain." *J Infect Dis.* 2019 Sep. 13; 220(8):1377-1387. doi: 10.1093/infdis/jiz073. PMID: 30799482; PMCID: PMC6743838.

TGF beta has been subject to special attention for its involvement in the inflammatory cascade oriented to the cytokine storm and for the possibility that its strong induction of fibrosis could be involved in potential future sequels of the COVID-19. Chen W. "A potential treatment of COVID-19 with TGF-β blockade." *Int J Biol Sci.* 2020 Apr. 21; 16(11):1954-1955. Doi: 10.7150/ijbs.46891. PMID: 32398962; PMCID: PMC7211163; Ghazavi et al. "Cytokine profile and disease severity in patients with COVID-19". *Cytokine.* 2020 Sep. 30; 137:155323. Doi: 10.1016/j.cyto.2020.155323. Epub ahead of print. PMID: 33045526; PMCID: PMC7524708; and Zhang et al. "Discharge may not be the end of treatment: Pay attention to pulmonary fibrosis caused by severe COVID-19." *J Med Virol.* 2020 Oct. 27. Doi: 10.1002/jmv.26634. Epub ahead of print. PMID: 33107641.

Neutrophil extracellular trap(s) (or NET(s)) are as described in American Heart Association, "Naturally occurring protein to block inflammatory response improved stroke recovery in mice" (Sep. 22, 2021), *Medical Express (Cardiology);* medicalxpress.com/news/2021-09-naturally-protein-block-inflammatory-response.html, the contents of which are incorporated herein by this reference.

An implantable medical lead is described in U.S. Pat. No. 8,442,653 to Gill (May 14, 2013) for "Brain Electrode," the contents of which are incorporated herein by this reference.

Both wireless non-invasive and/or implantable wire lead ("electrode") based means may be used to deliver the regeneration and healing promoting bioelectric signal(s) to target organs such as the brain.

A wireless, single lumen infusion pacing lead or infusion conduction wide array patch may all be used to deliver the regeneration signals and substances to the organ of interest to be treated or they may be used in combination.

A re-charging wand for use herein is preferably similar to the pacemaker re-charging wand developed by Alfred Mann in the early 1970's for recharging externally implantable pacemakers.

Bioelectric stimulation can be done with the described bioelectric stimulator, which can have a pacing infusion lead with, e.g., a corkscrew lead placed/attached at, e.g., the center of the tissue to be stimulated and/or treated.

The bioelectric stimulator is actuated and runs through programmed signals to signal the release of, e.g., GDF10. In such a method, the electrical signal may be measured three (3) mm deep into the tissue.

Relationship Between the Components:

The voltage signal generator is attached to the pacing infusion lead with, e.g., a brain electrode (Medtronic) (e.g., for bioelectric stimulation of the brain), or conductive polymer bandage or patch to the tissue or organ to be treated. An external signal programmer may be used to program the micro voltage signal generator with the proper signals for treatment including the GDF10 producing signal(s). The device battery may be re-chargeable with an external battery charging wand.

The essential elements are the voltage signal generator and the means for delivering the signal to the target tissue.

The signal generator may be external or internal. The transmission of the signal may be wireless, via liquid and/or via wires.

The tissue contact interface may be, e.g., a patch or bandage or may be via electrodes or leads. FDA cleared gel tape electrodes (Mettler) may be used for skin delivery. Electro acupuncture needles may be used to ensure the signals positively reach target tissues under the skin.

The invention is further described by the following illustrative Example(s).

EXAMPLE(S)

GDF10 Gene Expression in Porcine Brain Tissue.

Purpose: The purpose of this study was to quantify the expression of growth differentiation factor 10 in the brain of porcine tissue after stimulation with bioelectric signals.

Methods: The tissue pieces were stimulated with a Mettler stimulator for 20 minutes.

Figure 5:
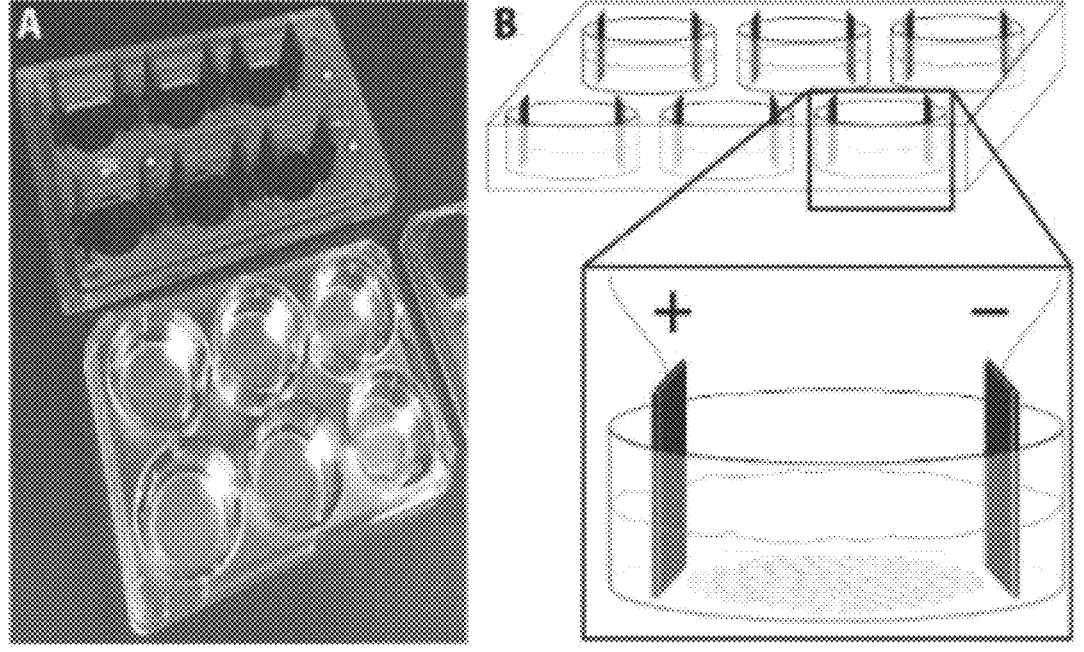
FIG. 5 depicts a bioelectric stimulation system.
Figure 6:
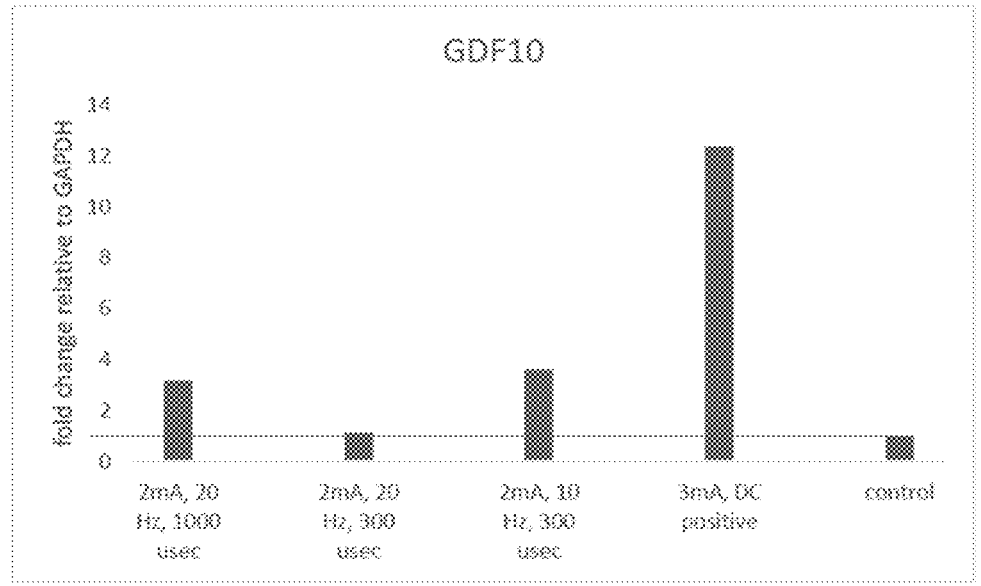
FIG. 6 is a graph depicting gene expression of GDF10 in porcine brain tissue stimulated at 2 mA to 3 mA with various types of bioelectric signals for 20 minutes.

FIG. 5 depicts a bioelectric stimulation system in which cells and/or tissue may be plated in each dish and cultured. Stimulation occurs using an electrode array (shown at the top of panel A), which is inverted and introduced into the 6-well dish where cells are grown. Each well receives uniform stimulation via a pair of carbon electrodes.

Thermo Fisher data analysis software may be used to calculate fold change/regulation using the delta-delta CT method, in which delta CT is calculated between the gene of interest (GOI) and an average of housekeeping genes (HKG), followed by delta-delta CT calculation (delta CT(experiment)-delta CT(control). Fold change is then calculated using the $2^{(-\text{delta CT})}$ formula.

Results of stimulation with a Mettler stimulator for 20 minutes:

| Bioelectric Stimulation Condition (20 minutes) | Fold Change |
|---|---|
| 2mA, 20 Hz, 1000 μs | 3.182146 |
| 2mA, 20 Hz, 300 μs | 1.140764 |
| 2mA, 10 Hz, 300 μs | 3.605002 |
| 3mA, DC positive | 12.38052 |
| Control | 1 |

REFERENCES (The contents of the entirety of each of which is incorporated herein by this reference.)

American Heart Association, "Naturally occurring protein to block inflammatory response improved stroke recovery in mice" (Sep. 22, 2021), *Medical Express (Cardiology)*; medicalxpress.com/news/2021-09-naturally-protein-block-inflammatory-response.html.

Chen W. "A potential treatment of COVID-19 with TGF-β blockade." *Int J Biol Sci.* 2020 Apr. 21; 16(11): 1954-1955. Doi: 10.7150/ijbs.46891. PMID: 32398962; PMCID: PMC7211163.

Ghazavi et al. "Cytokine profile and disease severity in patients with COVID-19". *Cytokine.* 2020 Sep. 30; 137:155323. Doi: 10.1016/j.cyto.2020.155323. Epub ahead of print. PMID: 33045526; PMCID: PMC7524708.

Jiang et al. "A guinea pig IFNA1 gene with antiviral activity against human influenza virus infection." *Front Biosci* (Landmark Ed). 2019 Mar. 1; 24:790-797. PMID: 30844713.

Kennedy et al. "Impaired innate, humoral, and cellular immunity despite a take in smallpox vaccine recipients." *Vaccine.* 2016 Jun. 14; 34(28):3283-90. Doi: 10.1016/j.vaccine.2016.05.005. Epub 2016 May 11. PMID: 27177944; PMCID: PMC5528000.

Kumar et al. "Human Sertoli cells support high levels of Zika virus replication and persistence." *Sci Rep.* 2018 Apr. 3; 8(1):5477. doi: 10.1038/s41598-018-23899-x. PMID: 29615760; PMCID: PMC5883016.

Limonta et al. "Fibroblast Growth Factor 2 Enhances Zika Virus Infection in Human Fetal Brain." *J Infect Dis.* 2019 Sep. 13; 220(8):1377-1387. doi: 10.1093/infdis/jiz073. PMID: 30799482; PMCID: PMC6743838.

Madhuri et al. "BCG vaccine and COVID-19: implications for infection prophylaxis and cancer immunotherapy." *J Immunother Cancer.* 2020 July; 8(2): e001119. Doi: 10.1136/jitc-2020-001119. PMID: 32636240; PMCID: PMC7342862.

McGowan et al. "Targeting the SphK-S1P-S1PR Pathway as a Potential Therapeutic Approach for COVID-19." *Int J Mol Sci.* 2020 Sep. 29; 21(19):7189. Doi: 10.3390/ijms21197189. PMID: 33003377; PMCID: PMC7583882.

Simone et al. "Intussusceptive angiogenesis in Covid-19: hypothesis on the significance and focus on the possible role of FGF2." *Mol Biol Rep.* 2020 October; 47(10): 8301-8304. Doi: 10.1007/s11033-020-05831-7. Epub 2020 Sep. 12. PMID: 32920756; PMCID: PMC7486971;

Songlin Li, et al., "GDF10 is a signal for axonal sprouting and functional recovery after stroke," *Nature Neuroscience,* 2015; doi:10.1038/nn.4146.

Zhang et al. "Discharge may not be the end of treatment: Pay attention to pulmonary fibrosis caused by severe COVID-19." *J Med Virol.* 2020 Oct. 27. Doi: 10.1002/jmv.26634. Epub ahead of print. PMID: 33107641.

U.S. Pat. No. 8,442,653 to Gill (May 14, 2013) for "Brain Electrode".

U.S. Pat. No. 9,700,596 to Carmichael et al. (Jul. 11, 2017) for "Locally released growth factors to mediate motor recovery after stroke".

U.S. Pat. No. 10,960,206 to Leonhardt et al. (Mar. 30, 2021) for "Bioelectric Stimulator".

US Patent Application Publication No. 20200000709 A1 (Jan. 2, 2020) for "Combination of Bioelectric Stimulator and Platelet-Rich Fibrin for Accelerated Healing and Regeneration"

U.S. Patent Application Publication US 20200289826 A1 to Leonhardt et al. (Sep. 17, 2020) for "Klotho Modulation".

U.S. Patent Application Ser. No. 63/237,682, filed Aug. 27, 2021, to Leonhardt et al. for "Modulation of Brain-Derived Neurotrophic Factor (BDNF)".

What is claimed is:

1. A method of stimulating an expression of growth differentiation factor 10 (GDF10) in a cell having a gene encoding GDF10, wherein the method comprises:

applying to the cell a first bioelectric signal of 2 mA to 3 mA direct current positive polarity;

measuring, at the cell to which the first bioelectric signal is being applied, the applied first bioelectric signal; and applying a separate bioelectric signal to the cell that upregulates expression of brain-derived neurotrophic factor (BDNF) in the cell, wherein the amount of GDF10 expression by the cell is enhanced by the first bioelectric signal.

2. The method according to claim 1, wherein the first bioelectric signal is 3 mA direct current positive polarity.

3. The method according to claim 1, wherein the cell is located in tissue selected from the group consisting of brain, inner ear, uterus, prostate, neural tissue(s), blood vessels, adipose tissue, spleen, liver, bone, cochlea, lung, testis, retina, and pineal gland.

4. The method according to claim 1, further comprising:

selecting a subject suffering from cerebral stroke, brain injury, paralysis, brain cancer, Alzheimer's disease, dementia, anxiety, Parkinson's, and/or essential tremors, and wherein the cell is located in tissue in the subject.

\* \* \* \* \*